(12) United States Patent
Pierce, II et al.

(10) Patent No.: US 11,061,147 B2
(45) Date of Patent: Jul. 13, 2021

(54) ACCURATE PHOTON DEPTH-OF-INTERACTION DECODING AND CALIBRATION OF MULTIPLEXED DETECTOR MODULES

(71) Applicant: University of Washington, Seattle, WA (US)

(72) Inventors: Larry A. Pierce, II, Seattle, WA (US); Robert S. Miyaoka, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 16/805,444

(22) Filed: Feb. 28, 2020

(65) Prior Publication Data
US 2020/0278456 A1    Sep. 3, 2020

Related U.S. Application Data (60) Provisional application No. 62/812,558, filed on Mar. 1, 2019.

(51) Int. Cl.
*G01T 1/16*    (2006.01)
*G01T 1/164*    (2006.01)
(Continued)

(52) U.S. Cl.
CPC .......... *G01T 1/1648* (2013.01); *A61B 6/4258* (2013.01); *G01T 1/202* (2013.01); *G01T 1/2928* (2013.01)

(58) Field of Classification Search
CPC ...... G01T 1/1648; G01T 1/202; G01T 1/2928
See application file for complete search history.

(56) References Cited

U.S. PATENT DOCUMENTS 5,171,998 A    12/1992 Engdahl et al.
5,504,334 A    4/1996 Jansen et al.
(Continued)

FOREIGN PATENT DOCUMENTS

JP    2005-308738 A    4/2005
JP    2008-51701 A    3/2008
(Continued)

OTHER PUBLICATIONS

T. Ling et al. (Investigation of Depth of Interaction Decoding for a Continuous Crystal Detector, T. Ling, Student Member, IEEE, T. K . Lewellen, Member, IEEE, R.S. Miyaoka, Member, IEEE, 2006 IEEE Nuclear Science Symposium Conference Record) (Year: 2006).*

(Continued)

*Primary Examiner* — Hugh Maupin
(74) *Attorney, Agent, or Firm* — Christensen O'Connor Johnson Kindness, PLLC (57) ABSTRACT

A method for calibrating a nuclear medicine tomography detector module using principal component analysis is based on the idea that calibration beam data lies on a one-dimensional path within the higher dimensional dataspace of output data. The module includes a weighted multiplexing circuit that generates a small number of multiplexed signals for each photon event. Calibration data for the module is generated and analyzed using several iterations of principal component analyses, to filter scattering events, noise, and other spurious signals. The direction of depth-of-interaction information has been found in the high-dimensional dataspace to be indicated by the primary principal component of the calibration data. The primary principal components, principal components from filtered datasets, intermediate thresholds, and DOI or inner product values are recorded for calibrating the module.

15 Claims, 10 Drawing Sheets

(51) Int. Cl.
   G01T 1/202   (2006.01)
   G01T 1/29    (2006.01)
   A61B 6/00    (2006.01)

(56) References Cited

U.S. PATENT DOCUMENTS

| | | | |
|---|---|---|---|
| 6,124,595 | A | 9/2000 | Engdahl et al. |
| 6,288,399 | B1 | 9/2001 | Andreaco et al. |
| 6,365,900 | B1 | 4/2002 | Mestais et al. |
| 6,459,085 | B1 | 10/2002 | Chang et al. |
| 6,528,793 | B1 | 3/2003 | Chen et al. |
| 7,129,496 | B2 | 10/2006 | Stearns et al. |
| 7,230,246 | B2 | 6/2007 | Hawman |
| 7,420,176 | B2 | 9/2008 | Motomura et al. |
| 7,601,963 | B2 | 10/2009 | Aykac et al. |
| 8,003,948 | B2 | 8/2011 | Haselman et al. |
| 8,309,932 | B2 | 11/2012 | Haselman et al. |
| 8,716,669 | B2 | 5/2014 | Miyaoka et al. |
| 2006/0163485 | A1 | 7/2006 | Stearns et al. |
| 2007/0253530 | A1 | 11/2007 | Mihailescu et al. |
| 2008/0224050 | A1 | 9/2008 | Thielemans et al. |
| 2008/0317194 | A1 | 12/2008 | Gagnon et al. |
| 2010/0044571 | A1 | 2/2010 | Miyaoka et al. |
| 2019/0000406 | A1* | 1/2019 | Liu .................. A61B 6/032 |

FOREIGN PATENT DOCUMENTS

| | | | |
|---|---|---|---|
| WO | 97/08569 | A1 | 3/1997 |
| WO | 2013/101956 | A1 | 7/2013 |

OTHER PUBLICATIONS

Peng Fan et al. ( 3D Positioning and Readout Channel No. Compression Methods for Monolithic PET Detector, Peng Fan, Tianpeng Xu, Zhenlei Lyu, Shi Wang, Yaqiang Liu and Tianyu Ma, 2016 IEEE) (Year: 2016).*

Miyaoka et al. (Multiplexing Strategies for cMiCE PET Detectors Roberts. Miyaoka, Senior Member, IEEE, William C.J. Hunter, Member, IEEE, Larry Pierce, 2012 IEEE Nuclear Science Symposium and Medical Imaging Conference Record (NSS/MIC) (Year: 2012).*

Astakhov, V., et al., "Effect of Depth of Interaction Decoding on Resolution in PET: A Simulation Study," IEEE Trans. Nucl. Sci. 50(5):1373-1378, Oct. 2003.

Borghi, G., et al., "Towards Monolithic Scintillator Based TOF-Pet Systems: Practical Methods for Detector Calibration and Operation," Phys. Med. Biol. 61:4904-4928, Jun. 2016.

España, S., et al., "DigiPET: Sub-Millimeter Spatial Resolution Small-Animal PET Imaging Using Thin Monolithic Scintillators," Phys. Med. Biol. 59 3405-3420, Jun. 2014.

Green, M.V., et al., "Experimental Evaluation of Depth-of-Interaction Correction in a Small-Animal Positron Emission Tomography Scanner," Mol. Imaging 9(6):311-318, Dec. 2010.

Jorge L., et al. "Experimental Validation of Improved 3D SBP Positioning Algorithm in PET Applications Using UW Phase II Board," Nuclear Instruments and Methods in Physics Research A, 838:103-108, Sep. 2016.

Maas M.C., et al., "Monolithic scintillator PET detectors with intrinsic depth-of-interaction correction," Phys. Med. Biol. 54:1893-1908, Mar. 2009.

Marcinkowski, R., et al., 2016 "Sub-Millimetre DOI Detector Based on Monolithic LYSO and Digital SiPM for a Dedicated Small-Animal PET System," Phys. Med. Biol. 61:2196-2212, Feb. 2016.

Morozov A., et al., 2015 "Iterative Reconstruction of Detector Response of an Anger Gamma Camera," Phys. Med. Biol. 60:4169-4184, 2015.

Pearson, K., "On Lines and Planes of Closest Fit to Systems of Points in Space," Philosophical Magazine 2:559-572, 1901.

Pedemonte, S., et al., "A Machine Learning Method for Fast and Accurate Characterization of Depth-of-Interaction Gamma Cameras," Phys. Med. Biol. 62:8376-8401, Oct. 2017.

Pierce et al., "Characterization of Highly Multiplexed Monolithic PET/Gamma Camera Detector Modules," Phys. Med. Biol. 63(7):075017, Mar. 2019.

Roweis, S.T., and L.K. Saul, "Nonlinear Dimensionality Reduction by Locally Linear Embedding," Science 290:2323-2326, Dec. 2000.

Schaart, D.R., et al., "SiPM-Array Based PET Detectors With Depth-of-Interaction Correction," IEEE Nuclear Science Symp. Conf. Record, Oct. 19-25, 2008, Dresden, Germany.

Shao, et al., "A Novel Method to Calibrate DOI Function of a PET Detector With a Dual-Ended Scintillator Readout," Med. Phys. 35(12), Dec. 2008.

Solovov, V. N., et al, "Position Reconstruction in a Dual Phase Xenon Scintillation Detector," IEEE Trans. Nucl. Sci. 59:3286-93, Sep. 2012.

Van Dam, H.T, et al, "A Practical Method for Depth of Interaction Determination in Monolithic Scintillator PET Detectors," Phys. Med. Biol. 56(13):4135-45, Jun. 2011.

Van Dam, I-1.T., et al., "Improved Nearest Neighbor Methods for Gamma Photon Interaction Position Determination in Monolithic Scintillator Pet Detectors," IEEE Trans. Nucl. Sci. 58(5)2139-2147, Nov. 2011.

Zernike, V.F., "Beugungstheorie des Schneidenverfahrens and Seiner Verbesserten Form, der Phasenkontrastmethode," Physica I, 689-704, 1934. "Diffraction Theory of the Knife-Edge Test and Its Improved Form, the Phase-Contrast Method" (English Translation).

Zhang, Y., et al., "A Practical Depth-of-Interaction PET/MR Detector With Dichotomous-Orthogonal-Symmetry Decoding," EJNMMI Physics 2(Suppl 1):A12, May 2015.

International Search Report dated May 18, 2010, issued in corresponding International Application No. PCT/US2009/061600, filed Oct. 22, 2009, 1 page.

Joung, J., et al., "cMiCE: A High Resolution Animal PET Using Continuous LSO With a Statistics Based Positioning-Scheme," Nuclear Instruments and Methods in Physics Research Section A: Accelerators, Spectrometers, Detectors and Associated Equipment 489(1-3):584-598, Aug. 2002.

Lee, K., et al., "Pragmatic Fully 3D Image Reconstruction for the MiCES Mouse Imaging Pet Scanner," Physics in Medicine and Biology 49(19):4563-4578, Oct. 2004.

Ling, T., et al., "Depth of Interaction Decoding of a Continuous Crystal Detector Module," Physics in Medicine and Biology 52(8):2213-2228, Apr. 2007.

Ling, T., et al., "Parametric Positioning of a Continuous Crystal PET Detector With Depth of Interaction Decoding," Physics in Medicine and Biology 53(7):1843-1863, Apr. 7, 2008.

Ling, T., et al., "Performance Comparisons of Continuous Miniature Crystal Element (cMiCE) Detectors," IEEE Transactions on Nuclear Science 53(5):2513-2518, Oct. 2006.

Maas, M.C., et al., "Experimental Characterization of Monolithic-Crystal Small Animal PET Detectors Read Out by APD Arrays," IEEE Transactions on Nuclear Science 53(3):1071-1077, Jun. 2006.

Miyaoka, R.S., et al., "Design of a Depth of Interaction (DOI) PET Detector Module," Proceedings of the IEEE Nuclear Science Symposium: Conference Record, Albuquerque, N.M., Nov. 9-15, 1997, vol. 2, pp. 939-943.

Miyaoka, R.S., et al., "Effect of Number of Readout Channels on the Intrinsic Spatial Resolution Performance of a Continuous Miniature Crystal Element (cMiCE) Detector," IEEE Transactions on Nuclear Science 54(5):1561-1567, Oct. 2007.

Miyaoka, R.S., et al., "Resolution Properties of a Prototype Continuous Miniature Crystal Element (cMiCE) Scanner," IEEE Transactions on Nuclear Science, 58(5):2244-2249, Oct. 2011.

Nichols, T.E., et al., "Spatiotemporal Reconstruction of List-Mode PET Data," IEEE Transactions on Medical Imaging 21(4):396-404, Apr. 2002.

Pierce, L.A., II, et al., "Multiplexing Strategies for Monolithic Crystal PET Detector Modules," Physics in Medicine and Biology 59:5347-5360, 2014.

* cited by examiner

FIG. 1
*(PRIOR ART)*

|   |   |   |   |   |   |   |   |
|---|---|---|---|---|---|---|---|
| 0 | 0 | 1 | 1 | 2 | 2 | 2 | 1 |
| 0 | 0 | 1 | 2 | 3 | 3 | 3 | 2 |
| -1 | -1 | 0 | 1 | 3 | 3 | 3 | 2 |
| -1 | -2 | -1 | 0 | 1 | 3 | 3 | 2 |
| -2 | -3 | -3 | -1 | 0 | 1 | 2 | 1 |
| -2 | -3 | -3 | -3 | -1 | 0 | 1 | 1 |
| -2 | -3 | -3 | -3 | -2 | -1 | 0 | 0 |
| -1 | -2 | -2 | -2 | -1 | -1 | 0 | 0 |

|   |   |   |   |   |   |   |   |
|---|---|---|---|---|---|---|---|
| 1 | 2 | 2 | 2 | 1 | 1 | 0 | 0 |
| 2 | 3 | 3 | 3 | 2 | 1 | 0 | 0 |
| 2 | 3 | 3 | 3 | 1 | 0 | -1 | -1 |
| 2 | 3 | 3 | 1 | 0 | -1 | -2 | -1 |
| 1 | 2 | 1 | 0 | -1 | -3 | -3 | -2 |
| 1 | 1 | 0 | -1 | -3 | -3 | -3 | -2 |
| 0 | 0 | -1 | -2 | -3 | -3 | -3 | -2 |
| 0 | 0 | -1 | -1 | -2 | -2 | -2 | -1 |

|   |   |   |   |   |   |   |   |
|---|---|---|---|---|---|---|---|
| 3 | 3 | 3 | 1 | 1 | 3 | 3 | 3 |
| 3 | 3 | 1 | 1 | 1 | 1 | 3 | 3 |
| 3 | 1 | 0 | -2 | -2 | 0 | 1 | 3 |
| 1 | 1 | -2 | -3 | -3 | -2 | 1 | 1 |
| 1 | 1 | -2 | -3 | -3 | -2 | 1 | 1 |
| 3 | 1 | 0 | -2 | -2 | 0 | 1 | 3 |
| 3 | 3 | 1 | 1 | 1 | 1 | 3 | 3 |
| 3 | 3 | 3 | 1 | 1 | 3 | 3 | 3 |

*FIG. 3C*

|   |   |   |   |   |   |   |   |
|---|---|---|---|---|---|---|---|
| -1 | -1 | -1 | -2 | -3 | -2 | -1 | 0 |
| -1 | -1 | 1 | 0 | -2 | -2 | 0 | 1 |
| -1 | 1 | 3 | 3 | 1 | 0 | 2 | 2 |
| -2 | 0 | 3 | 3 | 0 | -1 | 2 | 3 |
| -3 | -2 | 1 | 0 | -3 | -3 | 0 | 2 |
| -2 | -2 | 0 | -1 | -3 | -3 | -1 | 1 |
| -1 | 0 | 2 | 2 | 0 | -1 | 1 | 1 |
| 0 | 1 | 2 | 3 | 2 | 1 | 1 | 1 |

*FIG. 3D*

|   |   |   |   |   |   |   | 101E |
|---|---|---|---|---|---|---|---|
| 0 | -1 | -2 | -3 | -2 | -1 | -1 | -1 |
| 1 | 0 | -2 | -2 | 0 | 1 | -1 | -1 |
| 2 | 2 | 0 | 1 | 3 | 3 | 1 | -1 |
| 3 | 2 | -1 | 0 | 3 | 3 | 0 | -2 |
| 2 | 0 | -3 | -3 | 0 | 1 | -2 | -3 |
| 1 | -1 | -3 | -3 | -1 | 0 | -2 | -2 |
| 1 | 1 | -1 | 0 | 2 | 2 | 0 | -1 |
| 1 | 1 | 1 | 2 | 3 | 2 | 1 | 0 |

FIG. 3E

|   |   |   |   |   |   |   | 101F |
|---|---|---|---|---|---|---|---|
| 0 | 2 | 3 | 3 | 2 | 0 | -2 | -3 |
| -2 | 0 | 1 | 1 | 0 | 0 | -1 | -2 |
| -3 | -1 | 0 | 0 | 0 | 0 | 0 | 0 |
| -3 | -1 | 0 | 0 | 0 | 0 | 1 | 2 |
| -2 | -1 | 0 | 0 | 0 | 0 | 1 | 3 |
| 0 | 0 | 0 | 0 | 0 | 0 | 1 | 3 |
| 2 | 1 | 0 | 0 | -1 | -1 | 0 | 2 |
| 3 | 2 | 0 | -2 | -3 | -3 | -2 | 0 |

FIG. 3F

| | | | | | | | 101G |
|---|---|---|---|---|---|---|---|
| -3 | -2 | 0 | 2 | 3 | 3 | 2 | 0 |
| -2 | -1 | 0 | 1 | 1 | 1 | 0 | -2 |
| 0 | 0 | 0 | 0 | 0 | 0 | -1 | -3 |
| 2 | 0 | 0 | 0 | 0 | 0 | -1 | -3 |
| 3 | 1 | 0 | 0 | 0 | 0 | 0 | -2 |
| 3 | 1 | 0 | 0 | 0 | 0 | 0 | 0 |
| 2 | 0 | -1 | -1 | -1 | 0 | 1 | 2 |
| 0 | -2 | -3 | -3 | -2 | 0 | 2 | 3 |

ACCURATE PHOTON DEPTH-OF-INTERACTION DECODING AND CALIBRATION OF MULTIPLEXED DETECTOR MODULES

CROSS-REFERENCE TO RELATED APPLICATION

This application claims the benefit of Provisional Application No. 62/812,558, filed Mar. 1, 2019. The entire disclosure of said application is hereby incorporated by reference herein.

STATEMENT OF GOVERNMENT LICENSE RIGHTS

This invention was made with government support under R41 CA180191, CA136569, and EB002117 awarded by the National Institutes of Health. The government has certain rights in the invention.

BACKGROUND

The ability to produce images of the inside of a living organism without invasive surgery has been a major advancement in medicine over the last one hundred years. Imaging techniques such as X-ray computer tomography ("CT") and magnetic resonance imaging ("MRI") have given doctors and scientists the ability to view high-resolution images of anatomical structures inside the body. While this has led to advancements in disease diagnosis and treatment, a large set of diseases cause changes in anatomical structure only in the late stages of the disease, or never at all. This has given rise to a branch of medical imaging that captures certain metabolic activities inside a living body.

Positron emission tomography ("PET") and single-photon emission computed tomography ("SPECT") are in this class of medical imaging, referred to as nuclear medicine tomographic imaging.

Figure 1:
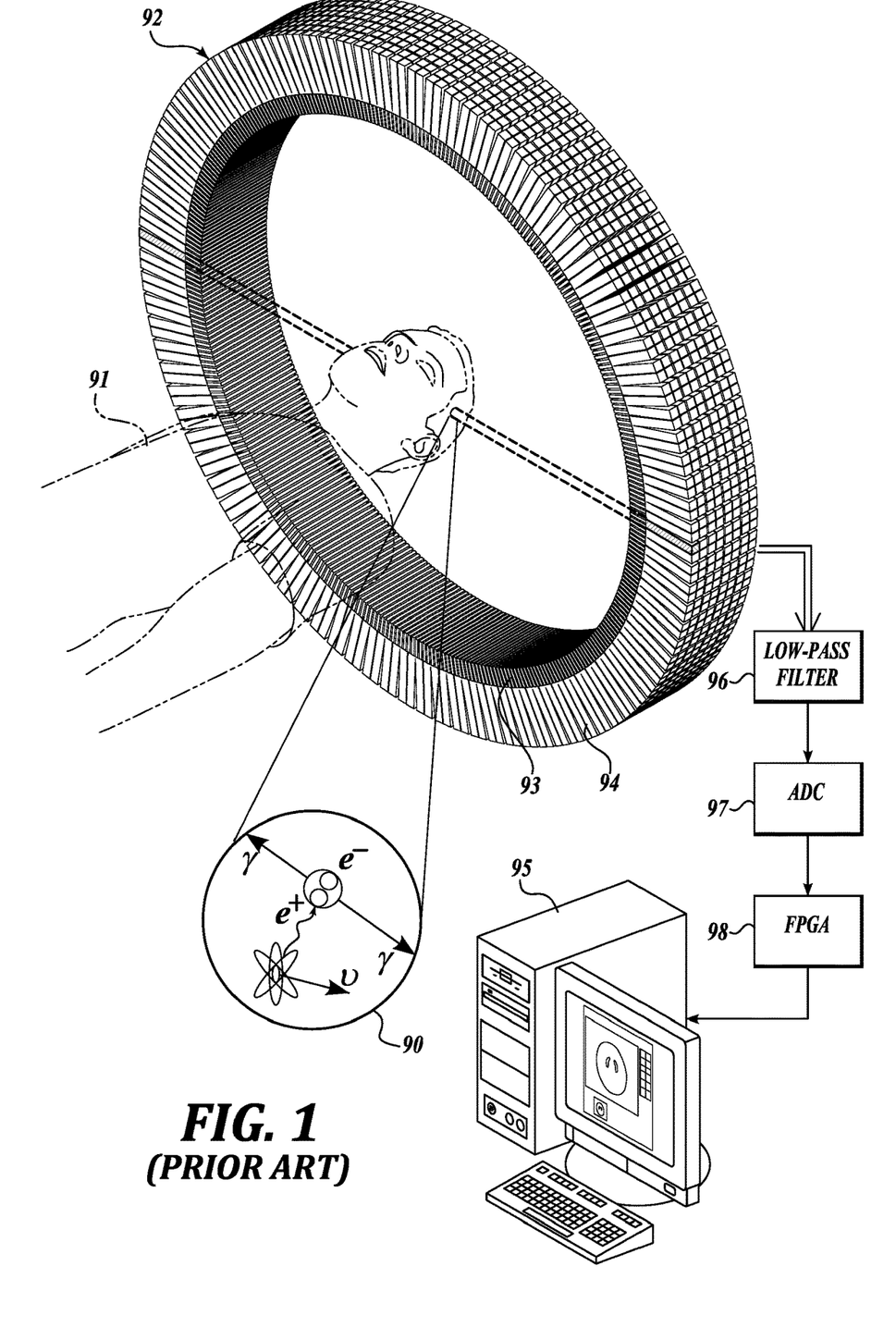
FIG. 1 is an environmental view showing a prior art positron emission tomography ("PET") system.

Referring to FIG. 1, to obtain a PET image, a radioactive tracer 90 comprising a radioactive isotope and a metabolically active molecule is injected into the body to be scanned 91. After allowing time for the tracer 90 to concentrate in desired tissues, the body 91 is suitably positioned to be imaged by the scanner 92. The radioactive decay event for tracers used in PET studies is positron emission. An emitted positron travels a short distance in the body tissue until it interacts with an electron. The positron-electron interaction is an annihilation event that produces two 511 keV anti-parallel photons. The scanner 92 is adapted to detect at least some of the photons from annihilation events.

The scanner 92 includes a ring of detector modules that detect the 511 keV photons. Front-end electronics process the signals generated by the detector modules. The detector modules include a crystal scintillator 93 and a photosensor or photosensor array 94. A scintillation event in the scintillator 93 converts 511 keV high-energy photons into many lower-energy photons, typically visible light photons. The photosensor arrays 94 detect the visible light photons and generate a corresponding electrical pulse. The photosensor pulses (for example, PMT pulses) are processed by front-end electronics to determine the parameters or characteristics of the pulse (i.e., energy, timing), e.g., a low-pass filter 96, analog-to-digital converter 97, and processor 98. Typically, the data is sent to a host computer 95 that performs tomographic image reconstruction to turn the data into a 3-D image.

Continuous miniature crystal element ("cMiCE") PET detector modules currently under development at the University of Washington use a 50×50×10 mm$^3$ continuous block of LYSO (lutetium-yttrium oxyorthosilicate) scintillation crystal coupled to a 65-channel multi-anode photomultiplier tube ("MA-PMT"). The MA-PMT has an 8×8 array of photosensors and a 65th output summation channel. Typically the estimation of interacting photon positions is performed using Gaussian maximum likelihood ("ML") techniques, as are well known in the art. The Gaussian ML position estimator requires a lookup table of the mean and variance or standard deviation of the PMT output signal for every (x,y,z) photon position within the crystal (segmented into discrete (x,y,z)-bins). The mean and variance are typically obtained by scanning a calibration beam of 511 keV photons at grid locations across the entrance face of the scintillation crystal, and recording the photosensor output.

The 511 keV calibration beam data can be contaminated in several ways, for example, by annihilation photons that have scattered off of the collimator prior to entering the crystal, by high-energy (1274 keV) gammas from the $^{22}$Na point source that passed through or scattered off of the collimator, by photons that scattered within the scintillation crystal, or by other types of random events. Identifying and rejecting scattered and random events in the calibration data is critical to the generation of accurate lookup tables for the Gaussian ML photon positioning algorithm. In some prior art systems scatter rejection for calibration data is performed using a two-step process. An initial scatter-rejection is performed via an Anger position estimate of the array of position-sensitive photosensor outputs. The Anger position estimate of each event is then compared to the Anger position estimate of the mean signal over all events and a median-distance threshold is used to reject events whose Anger position was too far from the mean position. A second filtering may then be performed, for example, using a 65th summed channel of the photosensor (e.g., PMT or other photosensor or combination of photosensors) to measure the energy spectrum for all photons from a given beam position. This spectrum may be used to define an energy window around the photopeak. Each event is then screened against this summed channel energy window as the second round of scatter-rejection.

Typically, after scatter rejection has been applied to the calibration data, only the (x,y)-position of each event from a given calibration beam is known. In some prior art systems the scintillation event z-direction (the depth-of-interaction, or DOI) is randomly distributed according to the Beer-Lambert distribution. The expected output signal for an interacting photon varies as a function of the DOI within the crystal, requiring that the detected events (after scatter-rejection) be sorted according to DOI in order to accurately localize the calibration photon interactions and create 3-dimensional lookup tables for the Gaussian ML position estimator.

Calibration photon DOI estimation in some prior art systems is performed by clustering the outputs for a given beam position according to the strength of the maximum channel from the array of position-channel outputs. This method makes use of the fact that the photons near the photomultiplier will have strongly localized signals and those further away will have their signal spread out more, resulting in a relatively lower peak channel signal. In other prior art methods, the DOI for a beam is estimated by fitting a Gaussian, Cauchy, parametric, or Lorentzian curve to each N×N-channel event and depth-sorting the events according to the fitting function parameters. These methods require knowledge of the shape of the N×N-channel signal in order to fit the DOI-estimation function to the signal output. These scatter rejection and depth estimation methods rely on having data from all output channels from the photosensor array.

In Pierce et al, *Multiplexing Strategies for Monolithic Crystal PET Detector Modules*, Phys. Med. Biol. 59 (2014) 5347-5360 ("Pierce et al."), which is hereby incorporated by reference in its entirety, a data-driven multiplexing scheme was proposed that uses the principal components of the expected output signal. As is known in the art, principal component analysis ("PCA") uses an orthogonal transformation of data to convert a set of possibly correlated variables into a set of values of linearly independent principal coordinates arranged in order from the principal coordinate with the largest variance, in decreasing order to the principal component with the smallest variance. The results of the analysis are typically discussed in terms of component or factor scores, and loadings (the weight by which the standardized original variables should be multiplied to get the component score).

The method disclosed by Pierce et al. assumes that general signal reconstruction for photon positioning is not necessary because each incoming photon will result in photosensor outputs that have a particular output 'shape', and not all output shapes are valid. Thus, the expected output data lie near a lower-dimensional manifold, e.g., within the 64-dimensional output vector space for an 8×8 array of photosensors. A dataset was collected by scanning a collimated beam across the detector input face. Taking the principal components of this dataset, each photon interaction output signal could be described as a weighted sum of only the most significant principle components. This results in acceptable signal reconstruction with as few as 8 principal component output channels.

However, the highly multiplexed PCA data disclosed by Pierce et al. do not preserve the information needed for scatter rejection and depth estimation. In Pierce et al. all of the 65-channel data is acquired for each scintillation event, and multiplexing of the 65-channel data was performed via simulation. It would be beneficial to reduce the amount of data that is acquired in PET calibration and imaging.

The method and system disclosed in Pierce et al. suffers from the hindrance that the 64-channel non-multiplexed data needed to be collected prior to affixing the multiplexing circuit in order to create accurate Gaussian ML lookup tables as well as for scatter rejection and depth estimation. In order to use the traditional scatter rejection and depth-estimation calibration methods with a PCA multiplexed method, the 65-channel (non-multiplexed) data would need to be acquired at calibration time in order to characterize the multiplexed detector response. This would require a 65-channel 'calibration mode' addition to the multiplexing circuitry, adding to the cost and complexity of the method.

For calibration of a detector module, it would be beneficial to create new scatter rejection and depth-estimation imaging systems that can work directly on highly-multiplexed signal output obtained from the calibration beam. There remains a need for continued improvements in the cost, efficiency, and accuracy of PET systems.

A new method and system are disclosed for PET imaging using highly-multiplexed datasets. The method works directly on the multiplexed dataset and greatly reduces the need to collect and process large, non-multiplexed data for the detector calibration.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for calibrating a nuclear medicine tomography detector module, for example, a PET module having a monolithic crystal with an entrance face and an opposite face, and an array of photosensors disposed on the opposite fact is disclosed. The method includes simulating the module, calculating output signals for each sensor in the array of photosensors in response to a simulated photon point source at each point in a three-dimensional grid of points within the monolithic crystal, and computing a set of principal components for the simulation dataset. A subset of the principal components is selected, and a corresponding multiplexing circuit is connected to the photosensor array. The multiplexing circuit is configured to receive output signals from each sensor in the array and to output one weighted sum of the received output signals for each selected principal component. For each location on a two-dimensional grid of points on the entrance face of the monolithic crystal a beam is directed into the detector crystal and weighted sums from the multiplexing circuit are recorded (the first dataset). The principal components of the first dataset are calculated and used to filter out scatter events, generating a calibration dataset. The primary principal component of the calibration dataset is calculated. For each datapoint in the calibration dataset an inner product of the datapoint with the primary principal component of the calibration dataset is calculated, and the calibration dataset is filtered based on the inner products to generate a reduced dataset. For datapoints in the reduced dataset the inner product may be used to assign a depth-of-interaction for the datapoint. Principal components of the reduced dataset are then calculated that are orthogonal to the primary principal component of the calibration dataset, and the data is transformed into a coordinate system defined by the primary principal component and the principal components of the reduced dataset. The transformed data is used to define threshold boundaries, and a calibration of the detector module is generated by recording the primary principal component, the principal components of the reduced dataset, the threshold boundaries, and at least one of the depth-of-interaction and the inner product data.

In an embodiment the array of photosensors comprises at least 64 photosensors.

In an embodiment the weights for each sensor are scaled and/or rounded.

In an embodiment the subset of principal components comprises not more than seven principal components.

In an embodiment the subset of principal components are selected by testing different combinations of a number of the principal components having the highest magnitude, and selecting the subset from the number of principal components.

In an embodiment the step of directing a beam of photons into the monolithic crystal comprises directing a collimated beam created using a $^{22}$Na gamma emitter.

In an embodiment the simulation calculates output signals for each sensor in the array for the simulated photon for a solid angle from the simulated photon to the detectors plus a specular reflection from an entrance face of the scintillation crystal.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Methods and systems are disclosed for the calibration of nuclear medicine tomographic imaging tomography systems, for example, positron emission tomography ("PET") or single-photon emission computed tomography ("SPECT") monolithic crystal modules, wherein the methods and systems include depth of interaction ("DOI") estimation and scatter filtering. The methods use weighted, highly multiplexed calibration data from the detector modules, eliminating the need to obtain and analyze the entire set of individual photosensor data for each scintillation event. The detector modules are configured to generate a small number of multiplexed outputs from the array of photosensors for the detector module. The weighted multiplexing scheme is based on a principal component analysis of a simulation dataset for the detector module, wherein the weighted multiplexed data includes information to enable estimation of the depth of interaction (DOI) for photonic events in the crystal.

Principal component analysis ("PCA") is a statistical method for converting potentially correlated data into a set of linearly uncorrelated variables referred to as principal components. The first, or primary principal component has the largest possible variance, the second principal component has the largest variance possible under the constraint that it is orthogonal to the primary principal component. Successive principal components are similarly defined in the order of largest variance subject to orthogonality to the preceding principal components. PCA uses an orthogonal transformation of data to generate linearly uncorrelated principal coordinates arranged in order from the principal coordinate with the largest variance, in decreasing order to the principal component with the smallest variance. PCA produces component or factor scores and loadings or weights. A new method is disclosed herein that provides a distinct technical advantage over the prior art. In particular the disclosed methods provide scanner data that includes DOI information and improved scatter filtering. The methods enable the calibration of a monolithic detector module without requiring the acquisition, manipulation, and storing of very large amounts of data that is required by prior art calibration methods.

Figure 4:
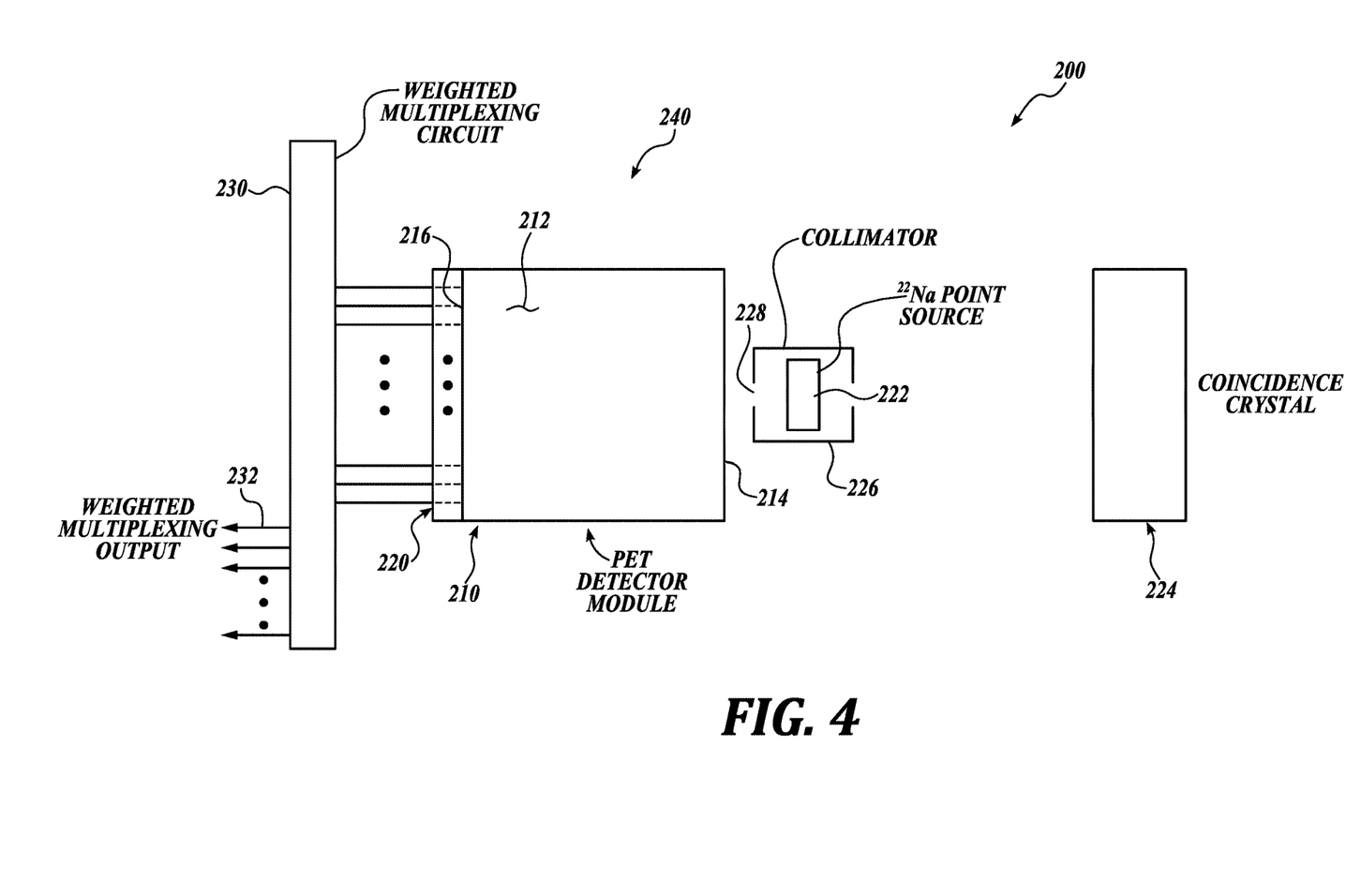
FIG. 4 illustrates a system for generating calibration data for a multiplexed detector module in accordance with the present invention.

A system and method are disclosed for calibrating a detector module 210, for example, a PET detector module, having a scintillation crystal 212 and an array of photosensors 220 (see FIG. 4). As described in more detail below, the method includes simulating the detector module 210 to generate a simulation dataset. The simulation dataset is analyzed using PCA to calculate the principal components of the simulation dataset, and a set of the principal components are selected. As is known in the art, each of the selected principal components defines a corresponding set of weights. A corresponding weighted multiplexing circuit 230 is constructed and connected to the detector module 210 to form a detector assembly 240, wherein the weightings are calculated using the selected principal components. The multiplexing circuit 230 is configured to generate one multiplexed output signal 232 for each of the selected principal component in response to photonic events in the scintillation crystal 212 detected by the array of photodetectors 220. A dataset is then generated by directing a high-energy beam into the scintillation crystal 212 on a grid of points on an entrance face 214 of the scintillation crystal 212 and recording the corresponding weighted multiplexed data. The dataset is then analyzed using PCA to generate a set of data that calibrates the detector module 210.

Figure 2:
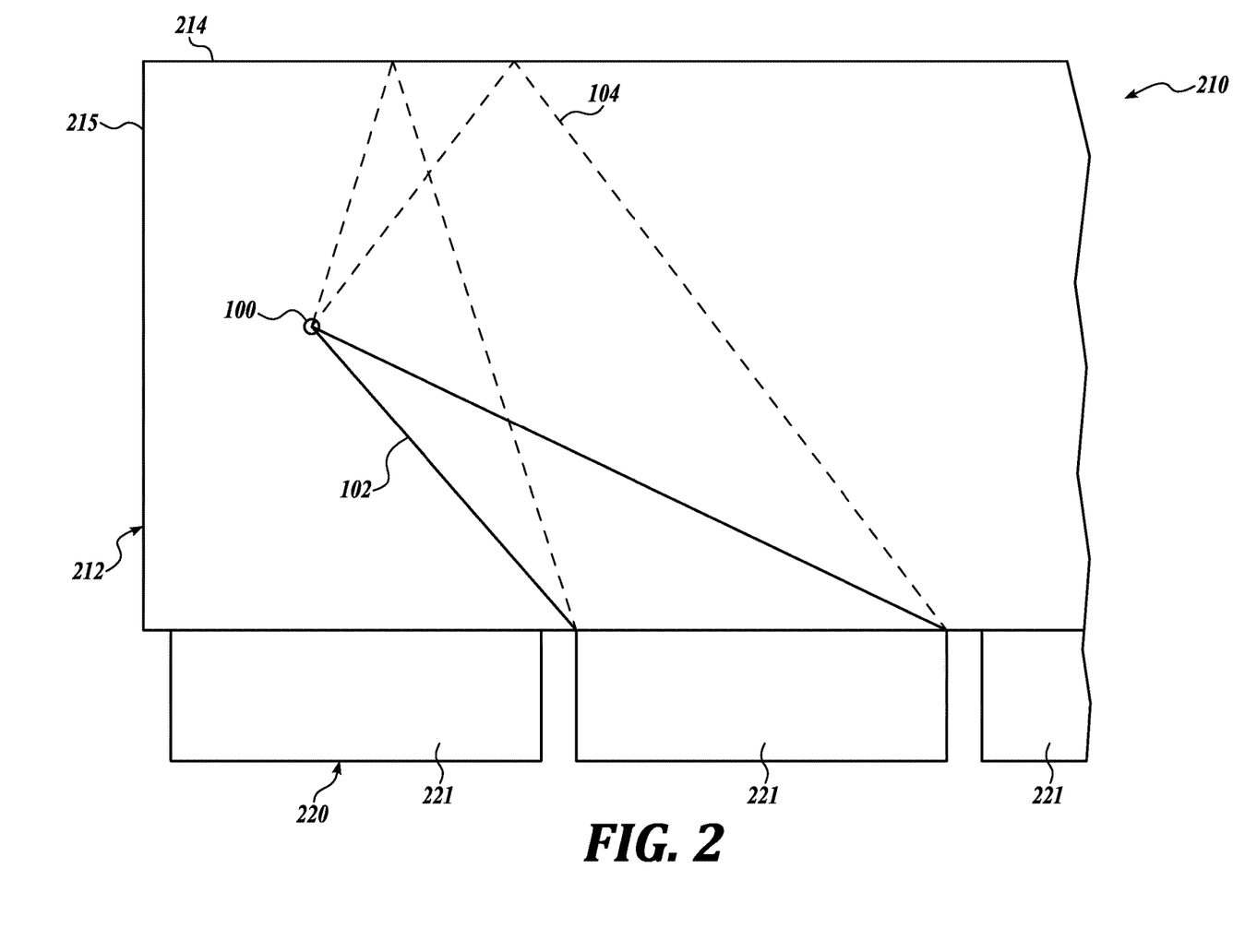
FIG. 2 shows schematically a detector module, and illustrates a simple modeling of a photon interaction within in the scintillation crystal.
Figure 3A:
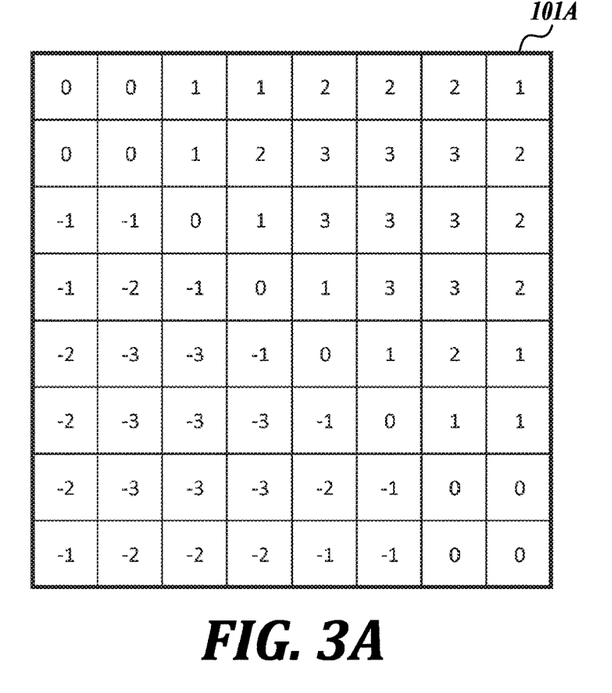
FIGS. 3A-3G show an example of a weighted multiplexing scheme for generating seven weighted multiplexed signals, each multiplexed signal including a weighted component from each sensor in an 8×8 array of photosensors.
Figure 3B:
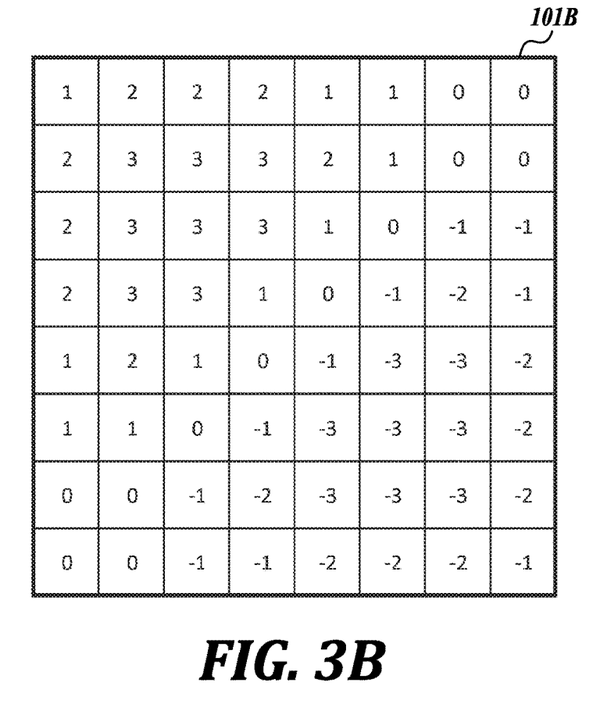
Figure 3C:
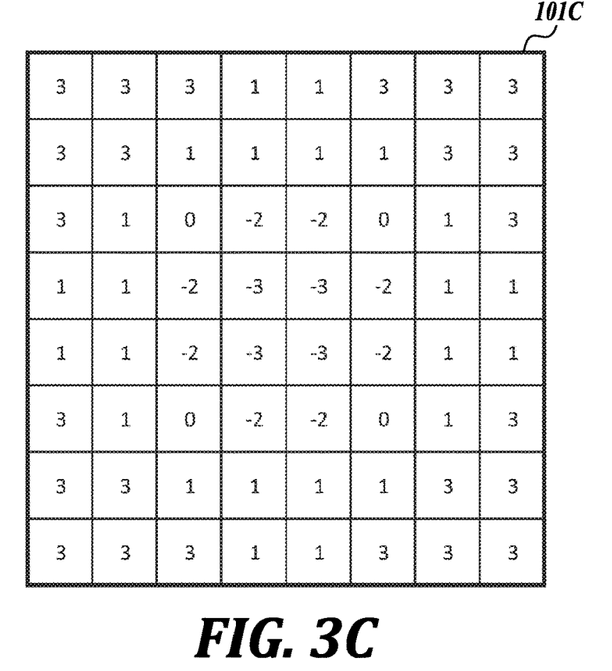
Figure 3D:
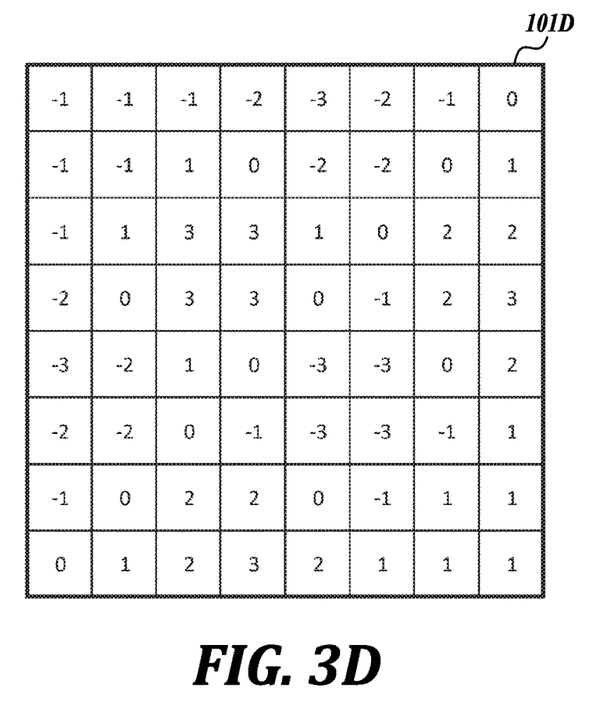
Figure 3E:
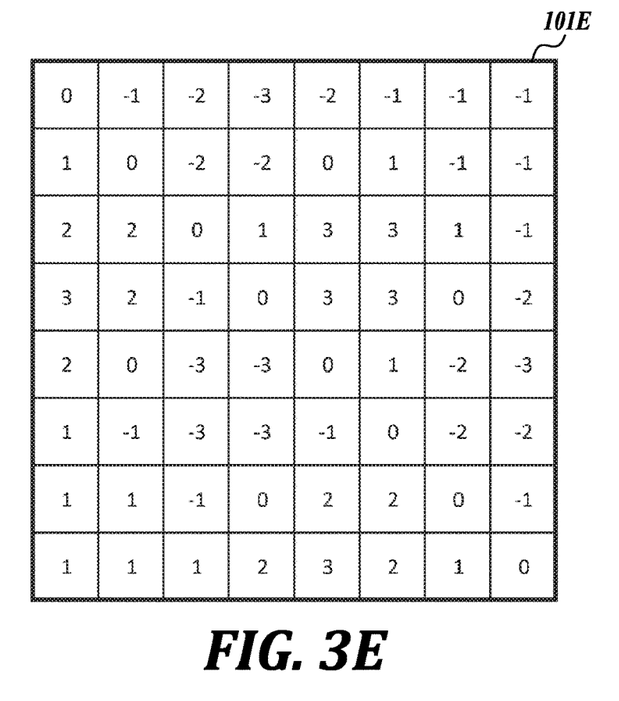
Figure 3F:
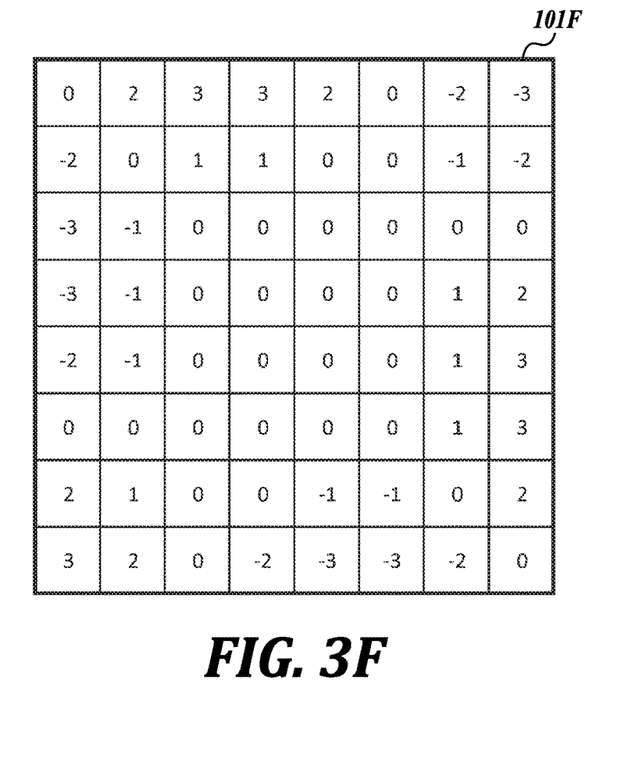
Figure 3G:
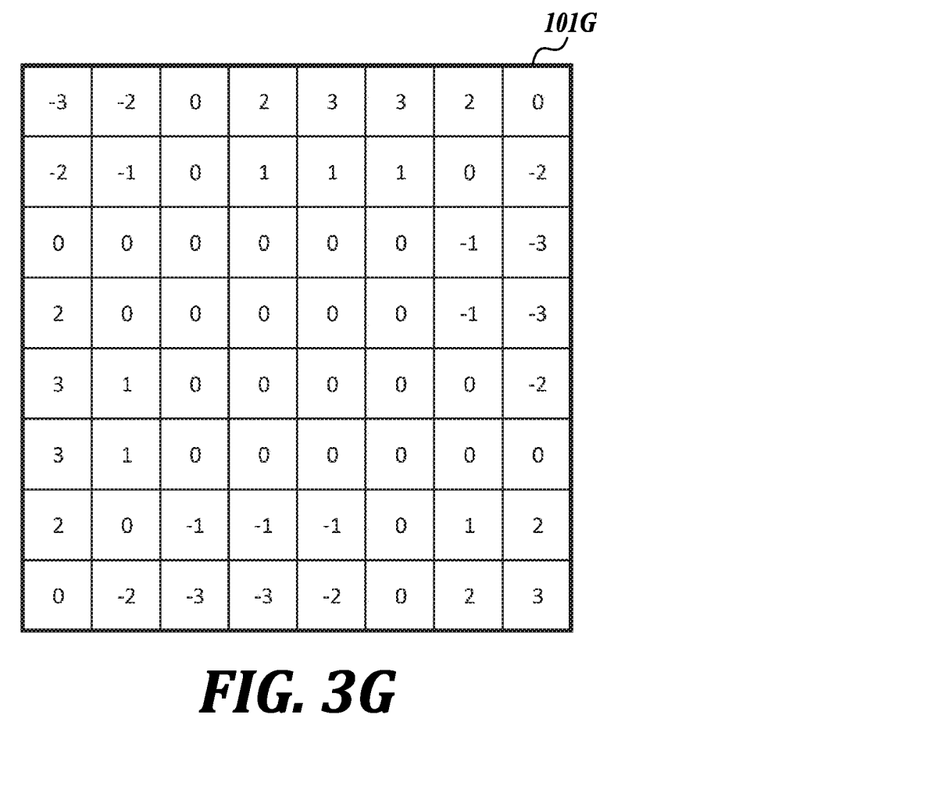

To determine the weights for the weighted multiplexing circuit 230 a simulation is performed to model the array of photosensor 220 outputs in response to photonic point sources in the scintillation crystal 212. FIG. 2 shows a simplified fragmentary view of the detector module 210, illustrating a point source 100 photon event in the crystal 212. In an exemplary method a 50×50×10 mm$^3$ scintillation crystal 212 having an 8×8 array 220 of 64 photosensors 221 is simulated. The photosensor 221 output is modeled as the solid angle 102 from the photon event 100 to the detector 221 plus the reflection 104 of the photon event 100 from the entrance face 214 of the crystal 212. In this embodiment, only single-acting photons are simulated, all with equal energy, and the entrance face 214 of the crystal 212 is modeled as a perfect specular reflector, with the edges 215 modeled as perfectly blackened. Isotropic photon point sources 100 are simulated on a cubic grid within the crystal 212 with a 1 mm spacing in all three dimensions. No noise is modeled. It will be appreciated by persons of skill in the art that more complicated models may be used to generate the simulation dataset.

The simulation data is then analyzed using PCA to calculate the principal components of the simulation dataset. For example, for an 8×8 array of 64 photosensors the PCA analysis produces 64 principal components each principal component having 64 elements (weights). A subset of the principal components is then selected. It has been found that as few as five to seven principal components are sufficient to produce good results to characterize an array of 64 photosensors. Optionally, the principal components may be scaled and/or rounded. For example, in a current embodiment the principal components are scaled and rounded so that only seven values are present in the principal component vectors, for example [−3, −2, −1, 0, 1, 2, 3]. The 16 most significant principal components from this dataset were tested via virtual multiplexing to determine which combination of output channels performed the best (visual inspection of the half-max contours, full-width at half-maximum (FWHM) of the half-max contours, minimal positioning bias, performance at the edge of the crystal, and agreement with the Lorentzian-fit depth estimation were all considered in this choice). A set of five principal components were chosen for the hardware implementation of a PCA multiplexed method (e.g., numbers 1, 2, 4, 8, and 9 in order of descending principal component value).

In one embodiment the same geometric simulation was run again using only photon interaction points within 3 mm of the edge of the crystal 212 (approximately one-half the width of one photosensor 221). This produced 64 principal components, which were also scaled and rounded to the 7 discrete values (as above), and two of the 'edge-specific multiplexing channels' were chosen to accompany the 5 channels previously chosen. This choice was based on the ability of the edge-specific multiplexing channels to enhance the performance of the detector 210 near the edge of the crystal 212 when used in addition to the 5 channels previously chosen.

In this example the seven sets of weights (5 principal components plus 2 edge-specific components) are coded into the resistive circuit 230. The circuit 230 is connected to the detector module 210 (see FIG. 4). After the PCA multiplexed circuit 230 was constructed, each of the 8×8 position-channels of the circuit input were probed with a known voltage (similar to the expected response from an incoming photon interaction from the photosensors) and the output of the seven multiplexed channels were recorded. The Euclidean norms of each of these 7-dimensional vectors from the test pulses was recorded as the pulse weights for later signal normalization.

Examples of seven principle component multiplexing circuits weightings 101A-101G are shown in FIG. 3, wherein the 8×8 grids correspond to the same array of 8×8 photosensors, and the numbers in the cells indicates a weighting factor calculated as described above.

Referring again to FIG. 4, an exemplary system 200 for generating weighted multiplexed calibration data for the detector module 210 will be described. In this embodiment the detector module 210 includes a scintillation crystal 212 having an entrance face 214, and a face 216 opposite the input face 214. An array of photosensors 220 engage the opposite face 216, and are configured to detect photons from the scintillation crystal 212. For example, in an exemplary system the array of photosensors 220 is an 8×8 array of photomultiplier tubes ("PMTs"). Other photosensor technologies may be used, including for example, silicon photomultipliers ("SiPMs"), avalanche photodiodes ("APDs"), and the like.

In this system 200, a thinly-collimated beam was created using a 0.5 mm diameter $^{22}$Na point source 222 collimated using a 4×4×20 mm$^3$ coincidence crystal 224 placed 11 cm beyond the point source 222. The point source 222 was 10 mm from the entrance face 214 of the scintillation crystal 212. A tungsten collimator 226 with a 2.0 mm diameter hole 228 was used to keep the point source 222 from flooding the rest of the detector module 210 to mitigate event pile up. This resulted in a beam that was 0.93 mm FWHM in diameter at the entrance face and 0.98 mm FWHM in diameter at the exit face of the scintillation crystal 212. This beam was scanned on a 1.52-mm grid across the input face 214 of the crystal 212, resulting in a 33-by-33 set of (x,y)-beam positions. The multiplexed signal for each output channel 232 from the multiplexing circuit 230 may optionally be normalized by dividing the recorded pulse weight to ensure that the maximum likelihood estimation is not dominated by any channel with larger voltage output.

The disclosed calibration method is predicated on the idea that the calibration beam data lies on a one-dimensional path (i.e., manifold) within the higher-dimensional space of the output signals. The most significant principal component should indicate the "depth direction" (in data space). However, in our dataset the largest data variance for each calibration beam is due to scattered and random photon interactions.

The method computes initial principal components using all of the data for a particular (x,y) location, and performs an initial density-threshold-based scatter rejection using these initial principal components. After filtering the data for the scatter rejection, the depth-direction is accurately found as the most significant principal component of the remaining data. Once the depth-direction is determined, a density-based threshold filtering is applied to the data in each dimension orthogonal to the depth-direction.

Figure 5A:
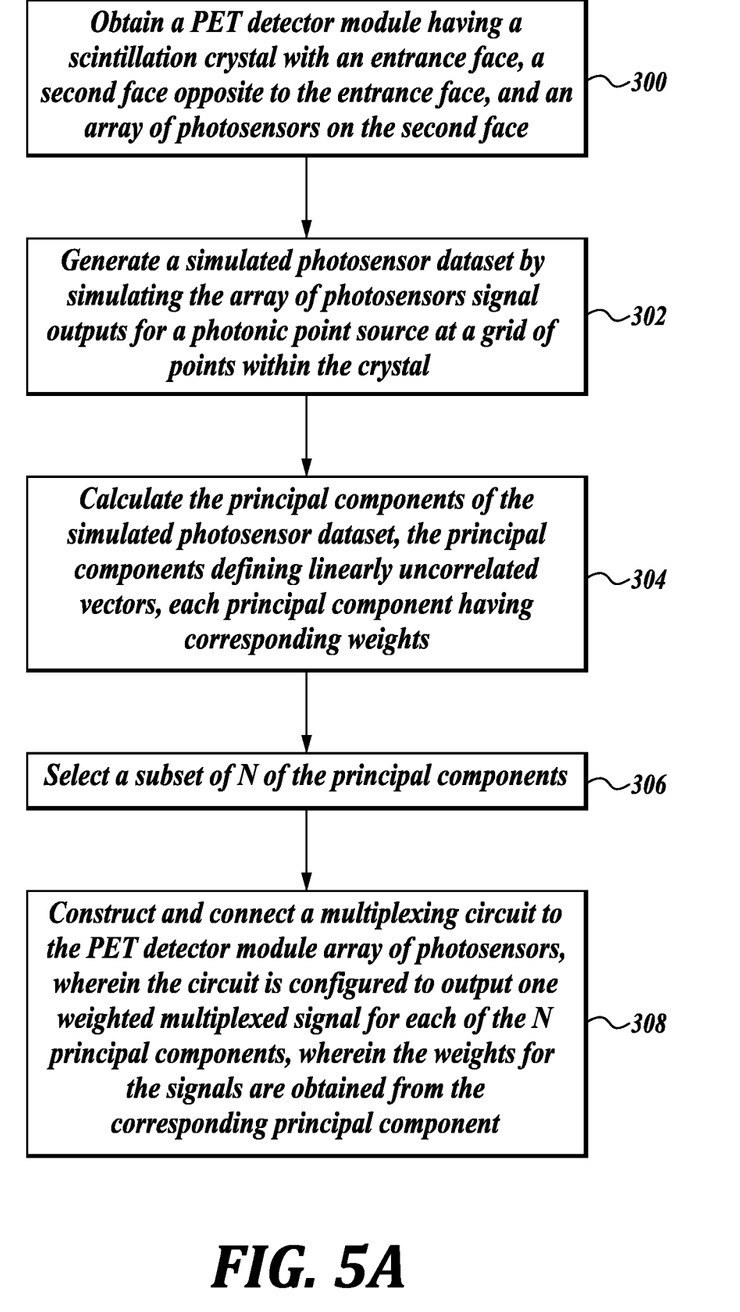
FIG. 5A is a flow chart illustrating a method of making a PET detector module with a multiplexing circuit that produces N weighted multiplexed signals from an array of photosensors in accordance with the present invention.
Figure 5B:
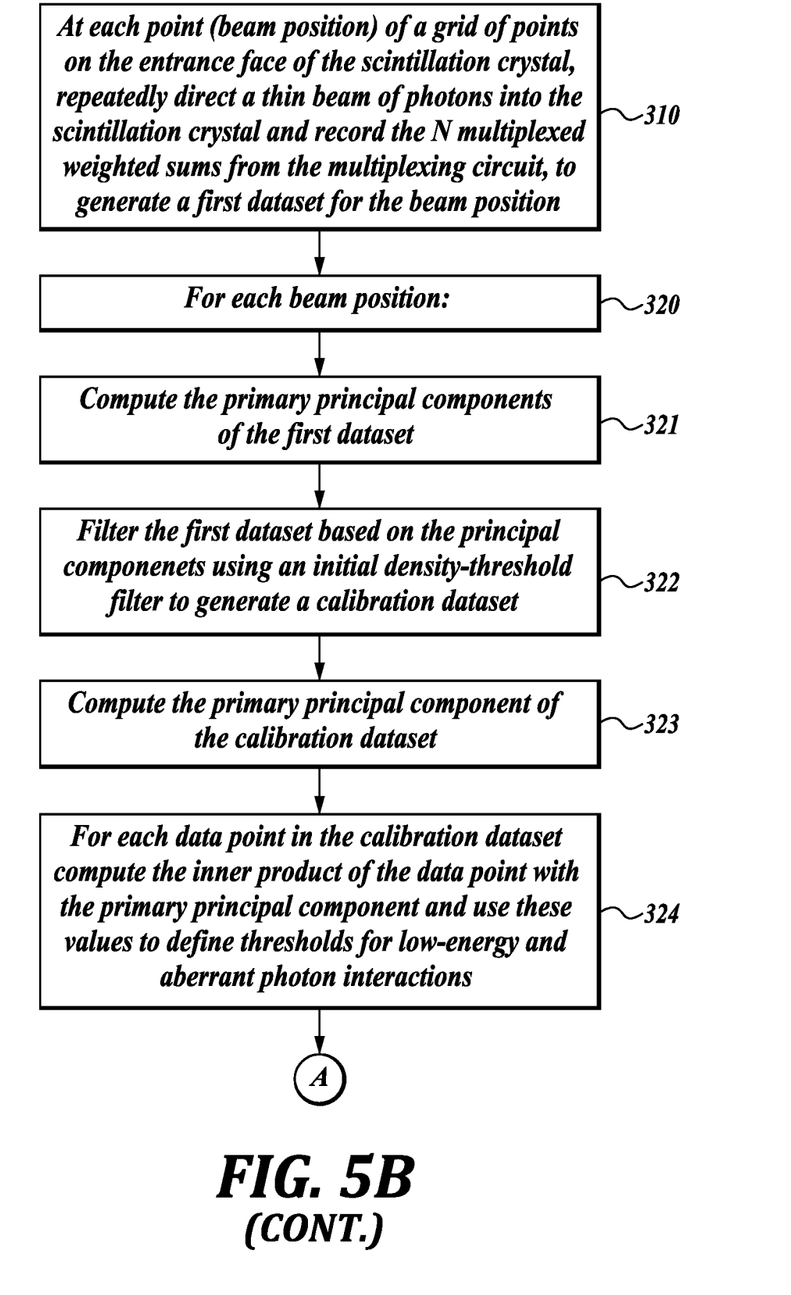
FIG. 5B is a flow chart illustrating a method for calibrating the PET detector module made by the method of FIG. 5A.

An overview of a currently preferred calibration method in accordance with the present invention will not be described. A detail description is shown in FIGS. 5A and 5B, and the related discussion. For each beam position a first application of PCA is applied, wherein the principal components of the calibration data are computed. The output data events are then transformed into the principal component coordinates via change-of-basis. The transformed channel values are analyzed to produce a density profile of events according to the principal component coordinate values. Upper and lower thresholds are defined as a fraction of the maximum density. Events that fall outside of this window are rejected as scattered events.

A second application of PCA is applied to the reduced (or calibration) dataset, and the principal components of the calibration dataset are computed to generate principal component vectors for the calibration dataset. The density of data points with respect to the most significant principal component are analyzed and upper and lower thresholds are determined according to this density profile. For example, the thresholds may be computed as a fraction of the maximum density. Events that fall below the lower threshold are rejected as low-energy scatter, events that fall above the upper threshold are rejected as high-energy $^{22}$Na gamma events.

The calibration data events are then projected onto the data subspace orthogonal to the most significant principal component vector, resulting in one less dimension spanned by the transformed data. The principal components of the projected data are then computed, in a third application of PCA. The data that passes the initial filtering are then transformed into the new principal component coordinates and a third round of density-based scatter rejection is performed. The thresholds previously defined are again used along that dimension, resulting in a bounding box.

Those events that lie within this bounding box are considered qualified events, and the inner product with the event data and the most significant principal component vector is used as a surrogate for the depth of interaction of that event (a higher inner product value implying a deeper depth). Depth bins are defined according to the expected fraction of interactions per bin, according to the Beer-Lambert distribution for 511 keV events in LYSO crystal with attenuation coefficient of 0.087 mm$^{-1}$. Once each qualified event is assigned a depth bin, the mean and variance or standard deviation σ, of the multiplexed signal is recorded for each depth bin.

In order to perform a faster 2-stage Gaussian maximum likelihood positioning, two sets of mean and variance or standard deviation lookup tables are recorded. The first set, referred to as $\mu_{initial}$ and $\sigma_{initial}$, uses multiple depth bins. The second set of lookup tables, $\mu_{final}$ and $\sigma_{final}$, uses multiple depth bins and is interpolated in the x- and y-directions to 0.30 mm bins using 2D spline interpolation. Each of the four lookup tables are smoothed using 3D Gaussian smoothing on each output channel.

When computing the $\mu_{initial}$ and $\sigma_{initial}$ lookup table values, the Euclidean norm of the events in each (x,y,z) bin is determined. Upper and lower thresholds are defined according to this density profile and recorded as $E_{x,y,z,lo}$ and $E_{x,y,z,hi}$.

The disclosed method yields an uncorrected resolution of approximately 1.17 mm from the 0.93-0.98 mm calibration beam for the 7-channel output experiments or 1.20 mm from the 5-channel experiments. The method exhibits detector resolution comparable to other methodologies, while still utilizing fewer output channels for positioning. The entire method (computation of lookup tables) takes about three minutes on a laptop computer (no parallel processing). Thus, the method can be used for detector calibration without the need for high-end computational equipment.

FIG. 5A is a flow chart illustrating an example of a method of designing and making a multiplexing circuit 230 for a detector module 240 in accordance with the present invention. In step 300 a detector module 210 having a scintillation crystal 212 with an entrance face 214, an opposite face 216, and an array of photosensors 220 on the opposite face is obtained. In step 302 a simulated dataset is generated by simulating point sources at a grid of points within the crystal 212. The simulation outputs a simulated signal for each of the sensors in the photosensor array 220. It is contemplated that the method will work with any number of photosensors, and with any type of photosensors, including photomultiplier tubes, and silicon photomultipliers. The principal components of the simulated dataset are then calculated 304. For example, for an N×N array of photosensors this results in N*N principal components with corresponding weights in each principal component.

A subset of the N principal components is then selected 306. The method has been found to be robust with regard to the particular N components selected. In a current embodiment various combinations of N components were tested to select the subset of N principal components. The weights may be rounded and scaled to simplify the multiplexing circuit 230. In step 308 the multiplexing circuit 230 corresponding to the selected principal components is constructed (or otherwise obtained) and connected to the photosensor array 220. The multiplexing circuit 230 is configured to receive the photosensor signals and to output one weighted multiplexed signal for each of the selected N principal components.

FIG. 5B is a flow chart of a method for calibrating a weighted multiplexing detector module in accordance with the present invention.

In this embodiment, a thin beam of photons are scanned into the crystal 212 (while attached to the photosensor) on a grid of (x,y) points on the entrance face 214 of the scintillation crystal 212, a plurality of times, to generate a first dataset (step 310). The first dataset will typically contain significant undesired data, for example, scattered events, noise, and the like. Useful data must be identified within the first dataset. For example, in a current embodiment the thin beam of photons was directed to each grid position 25,000 times, and corresponding data was collected for each event. For each beam position 320, the principal components of the first dataset are calculated (step 321). The first dataset is filtered according to the values of the principal components (step 322) using a density threshold, thereby reducing the dataset, and eliminating many scattered events. Determining suitable density thresholds may be done by trial and error, and is within the ability of persons of ordinary skill of the art. The filtered dataset is herein referred to as the calibration dataset. The calibration dataset is then analyzed using PCA, and the primary principal component of the calibration dataset is computed (step 323). A novel aspect of the present disclosure is the recognition that the primary principal component of the calibration dataset identifies the direction in higher-dimensional data space that indicated the depth of interaction of the detected photons.

For each datapoint in the calibration dataset compute the inner product of the datapoint with the computed primary principal component (from step 323) and use these inner products to define thresholds for low-energy and aberrant photon interactions (step 324). This step eliminates in-crystal Compton scatter. Filter data that are outside of the defined thresholds, to produce a reduced dataset, and use the inner products (from step 324) to assign a depth-of-interaction for the photon events in the reduced dataset (step 325). The inner products correspond to the depth-of-interaction.

Compute the principal components of the reduced dataset subject to the principal components being orthogonal to the primary principal component of the calibration dataset (step 326). Transform the data in the reduced dataset into a data space coordinate system defined by the primary principal component (from step 323) and the orthogonal principal components (from step 326) (step 327). Create histograms of each component of the transformed data and use the histograms to define threshold boundaries (step 328).

Record the primary principal component (from step 323), the inner products (from step 324) or equivalently the depth-of-interactions (from step 325), the principal components of the reduced calibration dataset (from step 327), and the threshold boundaries (from step 328), these data comprising the calibration of the detector module (step 329). The recorded data comprises the calibration of the detector module 210.

In a test embodiment of a detector module using a seven-channel multiplexing scheme (e.g., producing a 64:7 data compression ratio), the disclosed calibration method resulted in a scattered photon rejection rate that was a 55% improvement over a conventional summed signal energy-windowing method.

Example devices, methods, and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood other embodiments may include more or less of each element shown in a given Figure. Further, some of the illustrated elements may be combined or omitted. Yet further, an example embodiment may include elements not illustrated in the Figures. As used herein, with respect to measurements, "about" means+/−5%.

The embodiments of the invention in which an exclusive property or privilege is claimed are defined as follows:

1. A method for calibrating a nuclear medicine tomography detector module, the detector module comprising (i) a monolithic crystal having an entrance face and a second face opposite the entrance face and (ii) an array of photosensors comprising a plurality of photosensors disposed on the second face, the method comprising:

in a simulation, calculating output signals for each sensor in the array of photosensors in response to a simulated photon point source at each point in a three-dimensional grid of points within the monolithic crystal, wherein the simulated signals from each sensor comprises a simulation dataset;

computing a set of principal components of the simulation dataset, each principal component defining weights for each sensor in the array of photosensors;

selecting a subset of the set of principal components;

connecting a multiplexing circuit to the array of photosensors, wherein the multiplexing circuit is configured to receive output signals from each sensor in the array of photosensors and to output one weighted sum of the received output signals for each selected principal component, wherein weightings for the weighted sum are calculated from the principal component weights;

for each location on a two-dimensional grid of points on the entrance face of the monolithic crystal:
      directing a beam of photons into the monolithic crystal and recording weighted sums from the multiplexing circuit to generate a first dataset;
      computing principal components of the first dataset and filtering the first dataset based on the computed principal components to generate a calibration dataset;
      computing a primary principal component of the calibration dataset;
      for each datapoint in the calibration dataset, computing an inner product of the datapoint with the primary principal component of the calibration dataset and filtering datapoints based on the inner products, to generate a reduced dataset;
      for datapoints in the reduced dataset, using the corresponding inner product to assign a depth-of-interaction for the datapoint;
      computing principal components of the reduced dataset that are orthogonal to the primary principal component of the calibration dataset;
      transforming data in the reduced dataset into a coordinate system defined by the primary principal component and the principal components of the reduced dataset;
      using the transformed data to define threshold boundaries; and
      generating a calibration of the detector module by recording the primary principal component, the principal components of the reduced dataset, the threshold boundaries, and at least one of the depth-of-interaction and the inner product.

2. The method of claim 1, wherein the array of photosensors comprises at least 64 photosensors.

3. The method of claim 1, wherein the weights for each sensor are scaled.

4. The method of claim 1, wherein the weights for each sensor are rounded.

5. The method of claim 1, wherein the subset of principal components comprises not more than seven principal components.

6. The method of claim 1, wherein the subset of principal components are selected by testing different combinations of a number of the principal components having the highest magnitude, and selecting the subset from the number of principal components.

7. The method of claim 1, wherein the step of directing a beam of photons into the monolithic crystal comprises directing a collimated beam created using a $^{22}$Na gamma emitter.

8. The method of claim 1, wherein the simulation calculates output signals for each sensor in the array for the simulated photon for a solid angle from the simulated photon to the detectors plus a specular reflection from an entrance face of the scintillation crystal.

9. The method of claim 1, wherein the step of directing a beam of photons into the monolithic crystal comprises directing a collimated beam created using a $^{22}$Na gamma emitter.

10. A method for calibrating a nuclear medicine tomography detector module, the detector module comprising (i) a monolithic crystal having an entrance face and a second face opposite the entrance face and (ii) an array of photosensors comprising a plurality of photosensors disposed on the second face, the method comprising:

obtaining a set of principal components for the detector module;

connecting a multiplexing circuit to the array of photosensors, wherein the multiplexing circuit is configured to receive output signals from each sensor in the array of photosensors and to output one weighted sum of the received output signals for each selected principal component, wherein weightings for the weighted sum are calculated from the principal component weights;

for each location on a two-dimensional grid of points on the entrance face of the monolithic crystal:
      directing a beam of photons into the monolithic crystal and recording weighted sums from the multiplexing circuit to generate a first dataset;
      computing principal components of the first dataset and filtering the first dataset based on the computed principal components to generate a calibration dataset;
      computing a primary principal component of the calibration dataset;
      for each datapoint in the calibration dataset, computing an inner product of the datapoint with the primary principal component of the calibration dataset and filtering datapoints based on the inner products, to generate a reduced dataset;
      for datapoints in the reduced dataset, using the corresponding inner product to assign a depth-of-interaction for the datapoint;
      computing principal components of the reduced dataset that are orthogonal to the primary principal component of the calibration dataset;
      transforming data in the reduced dataset into a coordinate system defined by the primary principal component and the principal components of the reduced dataset;
      using the transformed data to define threshold boundaries; and
      generating a calibration of the detector module by recording the primary principal component, the principal components of the reduced dataset, the threshold boundaries, and at least one of the depth-of-interaction and the inner product.

11. The method of claim 10, wherein the array of photosensors comprises at least 64 photosensors.

12. The method of claim 10, wherein the weights for each sensor are scaled.

13. The method of claim 10, wherein the weights for each sensor are rounded.

14. The method of claim 10, wherein the subset of principal components comprises not more than seven principal components.

15. The method of claim 10, wherein the subset of principal components are selected by testing different combinations of a number of the principal components having the highest magnitude, and selecting the subset from the number of principal components.

* * * * *